US006687190B2

(12) United States Patent
Momich et al.

(10) Patent No.: US 6,687,190 B2
(45) Date of Patent: Feb. 3, 2004

(54) METHOD AND APPARATUS FOR CLINICAL TRIALS (76) Inventors: Robert Momich, 12-120 Quigley Road, Hamilton (CA), L8K 6L4; Michael E. Infuso, 1190 Royal York Road, Apt. 1, Toronto, Ontario (CA), M9A 4B3

( * ) Notice: Subject to any disclaimer, the term of this patent is extended or adjusted under 35 U.S.C. 154(b) by 164 days.

(21) Appl. No.: 10/024,477

(22) Filed: Dec. 21, 2001

(65) Prior Publication Data

US 2002/0064095 A1 May 30, 2002

Related U.S. Application Data (63) Continuation-in-part of application No. 09/359,322, filed on Jul. 23, 1999, now Pat. No. 6,335,907.
(51) Int. Cl.[7] .................. G04B 47/00; B65G 59/00; G07F 11/00; A61B 5/00
(52) U.S. Cl. ................ 368/10; 221/1; 221/2; 221/15; 600/300
(58) Field of Search .................. 368/10, 73, 250; 221/1, 2, 3, 15; 600/300

(56) References Cited

U.S. PATENT DOCUMENTS

| 5,642,731 A | * | 7/1997 | Kehr | 128/630 |
| 6,018,289 A | * | 1/2000 | Sekura et al. | 340/309.4 |
| 6,148,815 A | * | 11/2000 | Wolf | 128/205.23 |

* cited by examiner

Primary Examiner—Vit Miska
(74) Attorney, Agent, or Firm—Nancy E. Hill; Hill & Schumacher (57) ABSTRACT A method for conducting clinical trials for a medication uses a unique identifier, a clock and an smart memory associated with the medication. Information regarding a method of calculating a next take time is received. It is determined if an identifier field on the smart memory is empty and, if empty, the unique identifier is written onto the smart memory. If not empty, it is determined if the identifier in the identifier field is not the unique identifier and if not then exiting. On the other hand, if the unique identifier is present in the identifier field, then calculating the next take time; storing a next take time; and prompting at the next take time. The time on the clock is stored as a take time. In addition, a subject diary form is displayed and subject information in regard to subject diary form is stored.

23 Claims, 6 Drawing Sheets

Friday December 21, 2001        Clinical Trial: ZL29949
Participant Name: Nancy L. Jones DOSE # 2    10:00 A.M.  (2 more doses today)
- - - - - - - - - - - - - - - - - - - - - - - - - - - - - -
Please complete the following:

TAKE YOUR PULSE USING SUPPLIED MONITOR AND ENTER VALUE:

| 7 | 4 |                                    | DEFER |

Did you drink any of the following liquids within the last 2 hours?
(select all that apply)

- ○ coffee     ○ tea     ○ milk     ○ orange juice     ○ apple juice
- ○ tap water  ○ mineral water  ○ soft drink  ○ red wine
- ○ white wine  ○ beer Did you eat any of the following solids within the last 2 hours?
(select all that apply)

- ○ meat     ○ fish     ○ egg     ○ chicken     ○ bread
- ○ vegetables  ○ pasta     ○ rice     ○ nuts
- ○ salad (with oil dressing)     ○ cheese

METHOD AND APPARATUS FOR CLINICAL TRIALS

CROSS REFERENCE TO RELATED PATENT APPLICATION

This patent application is a continuation-in-part of to U.S. patent application Ser. No. 09/359,322 filed on Jul. 23, 1999 now U.S. Pat. No. 6,335,907 entitled PACKAGE WITH INTEGRATED CIRCUIT CHIP EMBEDDED THEREIN AND SYSTEM FOR USING SAME which is incorporated herein by reference.

FIELD OF THE INVENTION

This invention relates methods and apparatuses for use in association with clinical trials and in particular with methods and apparatuses that include confirming that the correct medication has been administered.

BACKGROUND OF THE INVENTION

The clinical trial phase in the development of a pharmaceutical product involves providing the developed drug to ever increasing numbers of subjects in test groups, and monitoring their reactions over an extended period. This monitoring is an integral part of the drug development process, as it provides the complex test bed of variables against which the pharmaceutical product must perform its desired effect.

During a typical trial phase I, a small number of healthy volunteers test the drug for safety and help to determine the proper dosage. The focus is on questions like how the drug is absorbed by the body, metabolized and excreted, and what is its duration of action. Phase I often lasts approximately one year. A typical phase III focuses on whether or not the drug actually works. It is used by 100 to 300 patients to study its effectiveness and any side effects, and usually lasts 2 to 3 years. Phase III focuses on side effects with a test patient base of 3,000 to 10,000. The effects of the drug over a long term, the proper dosage, and the range of side effects are the products of the analysis, and may take 3 to 4 years to complete Until very recently, the mountains of patient diary and case report form data associated with these trial phases have been collected and recorded only on paper during visits to Clinical Research Coordinators (CRCs) to obtain refills of trial medication. In addition to concerns regarding completeness and accuracy, the task of merely organizing and 'cleaning' this data, and preparing paper reports for submission to approval bodies, is formidable. This remains a major bottleneck to progress in the development of new drugs. This is the most complex and time-consuming part of drug discovery and development. The delays incurred in the checking, re-checking, entering and transmitting of data all translate into very significant delays in analysis. The often poor quality of the data results in trial analysis that is not as trustworthy as the FDA would like. Every day of delay costs drug companies millions of dollars. Up to 30% of pharma development budgets are spent on making sure collected trial data is accurate. The number of drug trials conducted is increasing steadily, so the trials must become more efficient in their use of research budgets.

A transition to electronic data capture is underway. Recently pharma companies have been investing in web based systems for entering trial data (CRFs). The fewer number of people that handle the data, the higher likelihood that it is 'clean'. By shortening the path from data entry to the clinical trial database, researchers can gain much faster access to data of a much higher quality. Increasingly researchers want real time access to the data so that they can react quickly to detected problems and make adjustments to the trial.

Drug companies are trying to standardize the data they collect on a global basis for their trials databases (making fields the same name, type, units etc. is essential when building a database). They must also re-engineer the processes they use to conduct the trials, along with the technologies. Changing one without the other can leave the results short of the intended improvement. When operating on a global basis, it is important not to assume a networking infrastructure that cannot be relied upon locally (e.g. telecom and data networks, Internet access, etc.).

Privacy remains an issue, but modern safeguards through data encryption can virtually eliminate or at least reduce the risk. Names and other personal identifying information can be completely removed from any communicated data. As banking moves to consumer web transactions backed by security, health care professionals are increasingly more accepting of electronic record keeping.

Accordingly it would be advantageous to provide a system for data collection that is easy to use and reliable. Further it would be advantageous if such a system is portable.

SUMMARY OF THE INVENTION

The present invention is a method for conducting clinical trials for a medication that uses a unique identifier, a clock and a smart memory associated with the medication. Information regarding a method of calculating a next take time is received. It is determined if an identifier field on the smart memory is empty and, if empty, the unique identifier is written onto the smart memory. If not empty, it is determined if the identifier in the identifier field is not the unique identifier and if not then exiting. On the other hand, if the unique identifier is present in the identifier field: then calculating the next take time; storing a next take time; and prompting at the next take time. The time on the clock is stored as a take time. In addition, a subject diary form is displayed and subject information in regard to subject diary form is stored.

The clinical trial subject prompter (CTSP) of the present invention provides a platform that integrates medication prompting and electronic patient diary forms (subset of case report forms) for use by clinical trial subjects. The CTSP helps to solve some of the problems in conducting clinical trials and helps to ensure compliance with dosing regimen instructions by the clinical trial subjects.

The CTSP enables Clinical Research Coordinators (CRCs) to enforce the entry of patient diary data with each dose, providing longitudinal (spanning time) depth to the data that supports analysis by investigators (patient diary data can include both subjective responses and parametric data like temperature, weight, heart rate, etc.). Further it enables the integration of non-trial medications with trial medications for both compliance and longitudinal diary data features. The data collected on the CTSP platform may be stored on a variety of media types and retrieved using a variety of connection technologies. The CTSP platform may be integrated into existing and future electronic data capture (EDC) architectures for the automation of clinical trial data management (e.g. Oracle Clinical database). The CTSP may be integrated with consumer prompting device described in detail in U.S. patent application Ser. No. 09/359,322 filed on Jul. 23, 1999 entitled PACKAGE WITH INTEGRATED CIRCUIT CHIP EMBEDDED THEREIN AND SYSTEM FOR USING SAME which is incorporated herein by reference and the CTSP complements it by extending its use into the clinical trial data management market.

Further features of the invention will be described or Will become apparent in the course of the following detailed description.

BRIEF DESCRIPTION OF THE DRAWINGS

The invention will now be described by way of example only, with reference to the accompanying drawings, in which.

DETAILED DESCRIPTION OF THE INVENTION

Pharmaceutical companies are now anxious to migrate to electronic patient diaries and case report forms (CRFs). Completion of these forms with the assistance of a computer greatly increases the quality and accuracy of the data, and eliminates the expensive and time consuming step of converting the data into electronic format for use in a modern clinical trial data management database system. These modern systems provide a comprehensive analysis environment to support the query requirements of multiple professionals in a secure, distributed setting.

U.S. patent application Ser. No. 09/359,322 filed on Jul. 23, 1999 entitled PACKAGE WITH INTEGRATED CIRCUIT CHIP EMBEDDED THEREIN AND SYSTEM FOR USING SAME which is incorporated herein by reference describes a system and specifications for software agents and smart labels that enable sophisticated medication prompting to a consumer. It provides a way to combat the problem of medication compliance without requiring training or device programming on the part of the consumer. It discloses a system that is easy for the consumer to use, that can be used in association with multiple medications and that can be integrated into existing portable devices such as a cell phone, hand held computer, personal organizers and the like.

Although U.S. application Ser. No. 09/359,322 solves a number of problems in association with personal medication use, clinical trial data collection poses a number of additional problems. However there are some similarities, for example the subjects are under the same pressure to follow medication directions, warnings, etc., and perhaps an even greater pressure because the medications involved are new and unpredictable. Compliance is a leading, major concern of those conducting medication trials, just as it is with FDA approved medications.

In addition to complying with a specific medication regimen, subjects in a clinical trial are also asked to monitor their own reactions and self-medication history to aid researchers in understanding the effects (both positive and negative) of the new medication. Compounding the complexity of the situation is that the subject may be taking other medications (probably approved) during the trial. Lifestyle differences can be an important variable in drug response as well. Therefore, every patient's self-medication history is unique and complex by nature.

This self monitoring can take the form of subjective evaluations (Do you feel weak? Do you feel pain anywhere? Is the pain more or less than before?) or parametric data (Take your body temperature. Take your pulse. Did you exercise since your last dose? Did you drink coffee?). As the trial investigators cannot be there while the subjects are taking the full course of their medication, they rely on the subjects to carefully record a log of all relevant data. As one might guess, the results of this are usually unreliable and disappointing. The quality of this data is critical to the success of a trial. The more accurate and rich the data collected, the easier it is for researchers to understand effectiveness, side-effects and necessary precautions that may be advisable. Improving the quality of this data translates directly into more effective clinical trials.

Visits to a trial site (whether that be the subject's regular physician's office, or a specific office established by the sponsor) are the setting in which Case Report Forms are completed by the CRC, and much of this data must come from memory on the part of the subject. Depending on memory over an extended period for a picture of a complex set of subjective and parametric results, especially when combined with different life styles and medications, leads to a very inaccurate and incomplete picture of the changes in a subject's condition To solve this problem, the CTSP system focuses on the needs of a clinical trial. The software agent described in U.S. application Ser. No. 09/359,322 is used in regard to the prompting, confirmation and recordation. In association with the step in the CTSP system in which the host device (PDA or cell phone or independent device or any other platform) prompts the subject to take a medication, there is an additional step to prompt the subject to respond to subjective and parametric questions designed by the trial sponsor and clinical investigator to produce an electronic patient diary. This information may be prompted either before or after the patient takes the medication. In addition this information may also be gathered at other times during the day. Responses to these questions are stored in conjunction with the compliance data, so a complete picture of when changes in subject condition occurred are available. Queries and graphs can be constructed that would reveal a time line that shows changes in condition mapped against particular doses, combinations of medications, subject actions (e.g. exercise, meals, etc,). The results of deferred or missed doses can be effectively tracked.

The CTSP system allows for flexibility in the presentation of these patient diary forms. They could be programmed by the investigators for presentation at selected time intervals, or only after a particular number of doses (e.g. after every $5^{th}$ dose, or every $2^{nd}$ day, etc.). The system could also respond to subject initiated requests to provide patient diary data.

Patient diary questions can appear on the CTSP at several points in the interaction with the subject. For example this information may be gathered during or integrated with the prompt to take a dose of medication; according to a schedule that is independent of the prompts to take a dose of medication; and/or randomly as initiated by the user. The prompting for completion of patient diary form may be at any specific point so desired by the trial designers; at initiation or completion of a round of medication; and/or at a specific time of day or other elapsed time. Further the subject may decide to provide patient diary data at any time such as when feeling any side effect or change in general condition.

During a trial site visit to obtain more medication, the CRC's have an opportunity to capture the patient diary data. During the visit the CTSP hosting device, which may be a PDA, cell phone or other independent portable electronic device, could be connected into whatever electronic data capture (EDC) system is being used to host the CRFs. This assumes that the CRFs are electronic, as it is unlikely that data would be converted to paper format once it is already electronic. Electronic CRFs would also facilitate the integration of the patient diary data into the CRF database, which is then updated during the visit. It may be connected via any appropriate means, including but not limited to Bluetooth, hard-wired, infra-red, or telephony. Alternatively the CTSP hosting device could be connected to another portable electronic hosting device (like a PDA) on which an electronic CRF, prepared by the CRC or another authorized third party, would reside and be used by the CRC during the site visit. This device (ePCRF) would later be connected to whatever electronic data capture (EDC) system is being used to host the CRFs for analysis (e.g. Oracle Clinical).

In addition to capturing the patient diary data, during this site visit, the clinical research coordinator could also have the opportunity to make some changes. For example ad-hoc changes to the patient diary forms may be made and/or the parameters (including dosing regimens, remedial actions, warnings, etc.) of the medication prompting encoding on the investigational product container(s) may be changed. Alternatively if this information is on some external source that is accessed remotely this information could be updated at any time.

The CTSP system of the present invention provides the user with a number of advantages. It allows for communication with trial participants via the CTSP regarding any aspect of the trial; patient diary questions presentation in multiple languages and also graphically; one way or two way immediate communication with trial participants (via any appropriate means, including but not limited to Bluetooth, hard-wired, infra-red, or telephony); real time adjustments to the patient diary questions if more sophisticated networks are available; and/or real time data collection whenever desired by the CRC, or continuously real-time, if the CTSP hosting device includes wireless communication capabilities.

The main components of the CTSP system are a host portable device and a software agent. In addition a software application is used to program the CTSP This may be done on a separate platform or the CTSP. The host portable device is capable of running the software agent and displaying the text and images of the forms (questionaires). The host portable device may be a cell phone, PDA or other independent portable electronic device that can read and write onto a smart memory that is associated with the medication. Smart memory is used to indicate electronically readable and writeable memory which includes but is not limited to integrate circuit chips, photonic crystals and the like. The read and write capabilities may be contact or contactless and may include a smart card reader/writer. The host device may electronically communicate with other devices in the solution architecture in one or more possible ways. For example it may be hard wired connections (e.g. cable or cradle); use Bluetooth or other short range wireless connection technologies; use long range wireless connection (including telephony); or use smart card/smart label contact or contactless reader/writer. The host device could electronically store data in one or more possible ways. For example it could store data on a smart label (on the medication package); on a smart card that is inserted into the device (contact type) or brought close to the device (contactless type); on an IC or other memory in the device; or transmit it directly to the trial site host computers via a wireless telephony connection; or a combination thereof.

The software agent would include all of the capabilities described in U.S. patent application Ser. No. 09/359,322 and incorporated herewith by reference as well as the capability to displays text forms with menu choices and/or text entry fields for response and displays graphic images that are selectable as a response choice.

The software application is for designing the patient diary (and optionally the CRF forms) and may be on a personal computer. The software application is for generating the application executable code for loading onto the designated portable electronic device platform.

Figure 1:
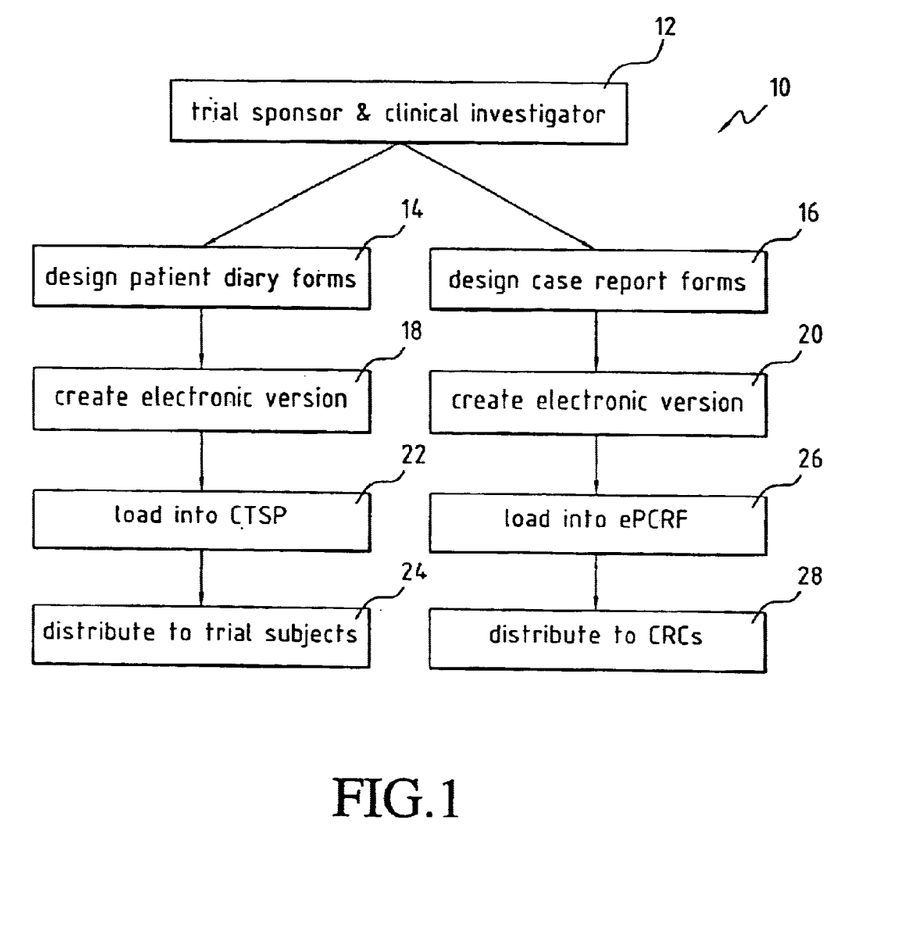
FIG. 1 is a flowchart showing setup and distribution of clinical trial subject prompter of the present invention and electronic portable case report form (ePCRF)

The CTSP system will now be described in more detail in relation to the flow charts. Referring to FIG. 1 the steps for setting up and distributing the clinical trial subject prompter (CTSP) and the electronic portable case report form (ePCRF) is shown generally at 10. The trial sponsor and clinical investigator design the trial protocol 12 and associated patient diary forms 14 and case report forms (CRFs) 16.

An electronic version of patient diary forms 18 and preferably an electronic version of the CRFs 20 are prepared using the software application. These are prepared using a graphical user interfaced application that facilitates the easy preparation of an electronic version of the patient diary forms and CRFs in an executable format particular to the portable electronic device platform such as a PDA or cell phone with large screen or other portable device. The software application provides an interface for building controls into the presentation of patient diary questions using a pallet of graphic icons. Further the software application enables the designer to set the precise manner in which the diary forms or CRFs are presented, including the integration of layers of dialog that branch within response choices. Further the software platform allows the CRC to set compliance management parameters.

The CTSPs are then loaded 22 with electronic patient diary forms and any other trial identification information such as trial identification codes. The forms and other information may be loaded via trial participant smart card, or via the smart medication package equipped with sufficient memory to contain the electronic version of the patient diary form; or via a wireless or other electronic connection. Optionally, the smart medication package label could contain a pointer to the electronic patient diary forms located on a remote site, and the wireless CTSP would retrieve the initial and subsequently updated forms through a network including the Internet or any subset or derivation thereof. Optionally, the smart medication package label could contain a pointer to a remote site on the network to retrieve all the compliance management parameters (as mentioned in the earlier patent). The CTSPs are then distributed to trial subjects 24.

If used, the electronic CRFs are loaded 26 onto a portable device, for example an ePCRF for use by CRCs during subject site visits. Thereafter the ePCRFs are distributed 28 to the CRCs.

Figure 2:
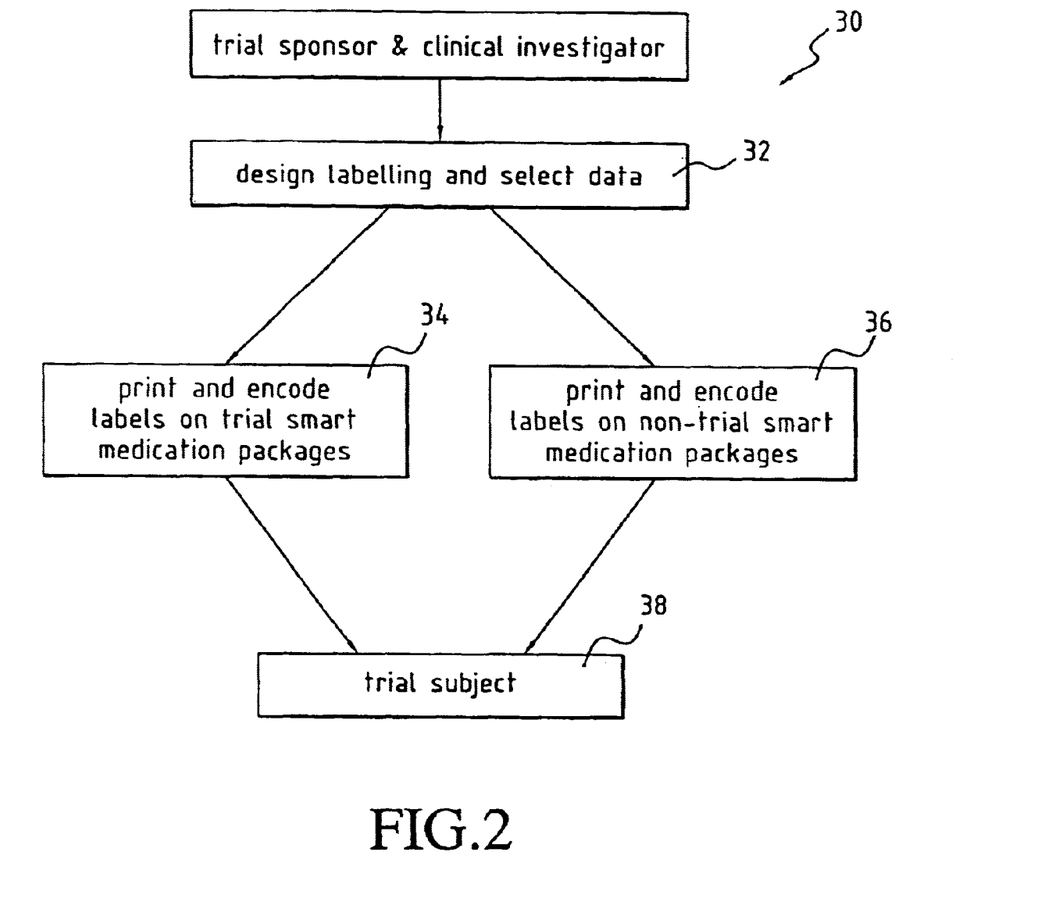
FIG. 2 is a flowchart showing setup of smart medication packages for use in association with the clinical trial subject prompter.

The steps for setting up the smart medication package for use in association with the trial is shown generally at 30 in FIG. 2. The trial sponsor and clinical investigator design labelling to be attached to investigational product container (s) and select data to be encoded on product container smart label 32. The data includes data to support medication prompting and other trial identifying information, like medication batch id. Product container sticky labels are printed and smart medication labels are encoded and placed on investigational product containers by CRC 34, Optionally, product container smart medication labels for medications outside the trial are printed and encoded and placed on subject's product containers by CRC 36. This would allow non-trial medications to be integrated with trial medications for management by the CTSP. The product containers are then distributed to trial subjects by CRC 38.

It will be appreciated by those skilled in the art that wherever we refer to information on a smart label or smart chip or in association with the CTSP or patient diary forms it could alternatively be a pointer that would connect the user to information on a remote site on a network, including the Internet or a subset or derivation thereof.

Figure 3:
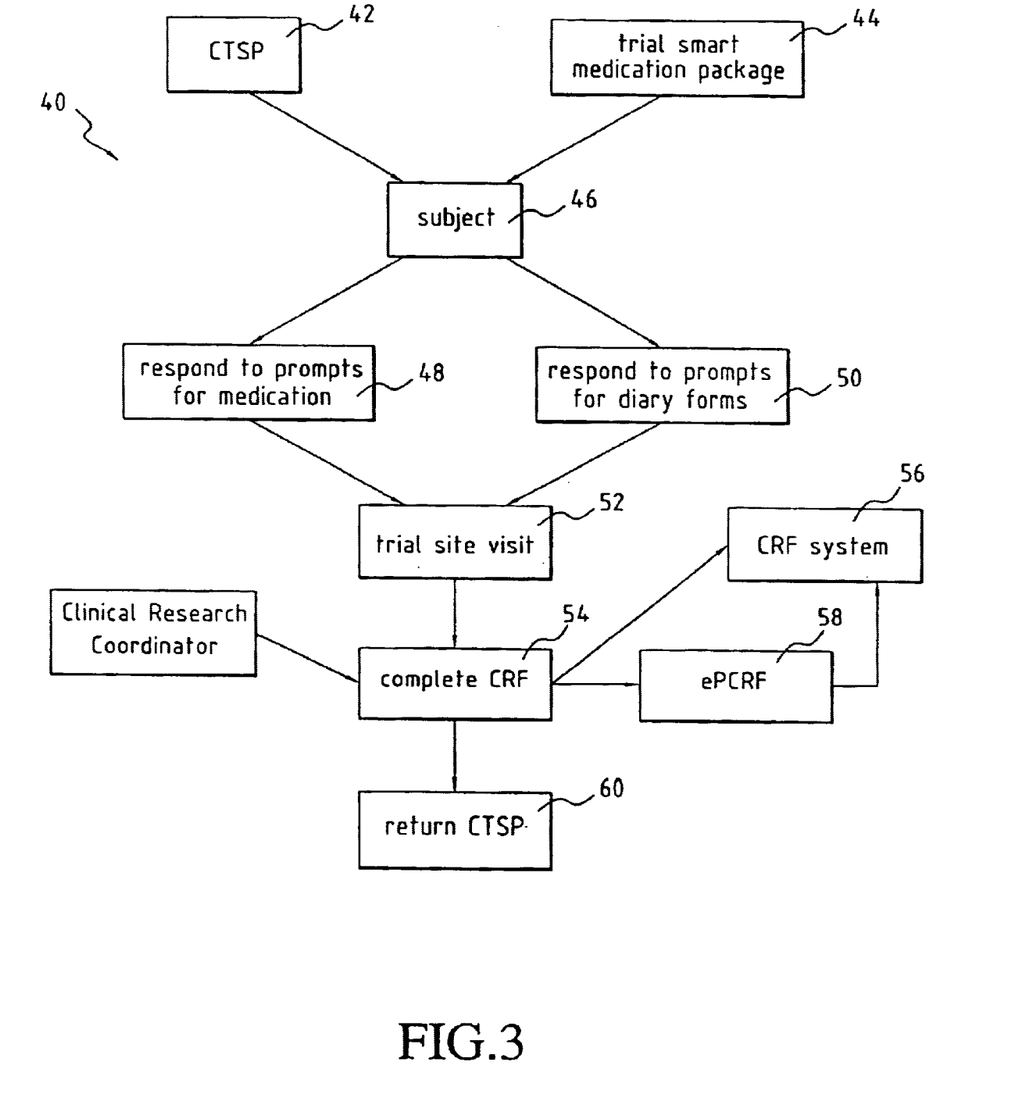
FIG. 3 is a flowchart showing use of clinical trial subject prompter by trial subject and clinical research coordinator.

The use of CTSP (Clinical Trial Subject Prompter) by trial subject and Clinical Research Coordinator (CRC) is shown generally at 40 in FIG. 3. After receiving the CTSP 42 along with the first package 44 of the trial investigational product, subject 46 follows the steps with regard to medication prompting 48 set out in U.S. patent application Ser. No. 09/359,322 and incorporated herewith by reference. In addition the subject 46 follows the following steps. The CTSP prompts for diary forms 50 and whenever a patient diary form is presented on the screen of the CTSP, the subject should respond to the questions in the form. If a particular question cannot be answered (e.g. if the question asks the subject to record his body temperature and a thermometer cannot be located temporarily), the DEFER option (if appropriate) would be available, and the question would be presented again according to the selected time frame for deferral within the deferral tolerances that had been set by the trial sponsor and clinical investigator. The patient diary forms are presented as specified by the trial sponsor and clinical investigator designing the trial, including during prompting for medication, or according to a schedule that is independent of medication prompting (e.g. first dose, fifth dose, last dose, every $10^{th}$ dose, etc.). In the event of failure to complete a particular question AND if so desired by the investigators, it is possible to halt the CTSP medication prompting and direct the subject to contact the CRC or other administrator for further directions.

The CTSP prompts subject when a refill of the investigational product is necessary, and this would in most cases require a visit 52 to the trial site for a consultation with a CRC and completion of a CRF (optionally the CTSP could be polled remotely for all patient diary data captured, and/or electronically signal the CRC that a refill is needed and the refill could be sent by the CRC without the necessity of a site visit).

The CRC or other medical staff responsible for conducting a trial site visit completes a Case Report Form (CRF) 54. If an ePCRF is not used, then the data from the patient diary on the CTSP is either manually or electronically entered into the CRF data base system (an automatic connection synchronized by the software) 56. If the CRF is provided electronically on a portable device (e.g. a PDA), the ePCRF device would electronically retrieve the patient diary information from the CTSP and integrate it into the CRF 58. The remainder of the CRF data is entered by the CRC (or assigned medical staff). As a result of feedback or other analysis during a trial it may be desirable to make ad-hoc adjustments to the patient diary form and medication regimen on the smart medication packages or on the remote site; in that case: the trial sponsor and clinical investigator make adjustments to the electronic patient diary form and medication regimen parameters (the medication regimen parameters that were identified and detailed in the earlier patent); adjusted forms are transferred to the CTSP directly during site visit (or via trial participant smart card or other electronic connection at any time); and where applicable adjusted medication regimen parameters are used during printing and encoding of next batch of trial investigational product containers. The subject is given the next package of the trial investigational product and their CTSP and the process repeats until the subject's trial participation is completed 60.

Figure 4:
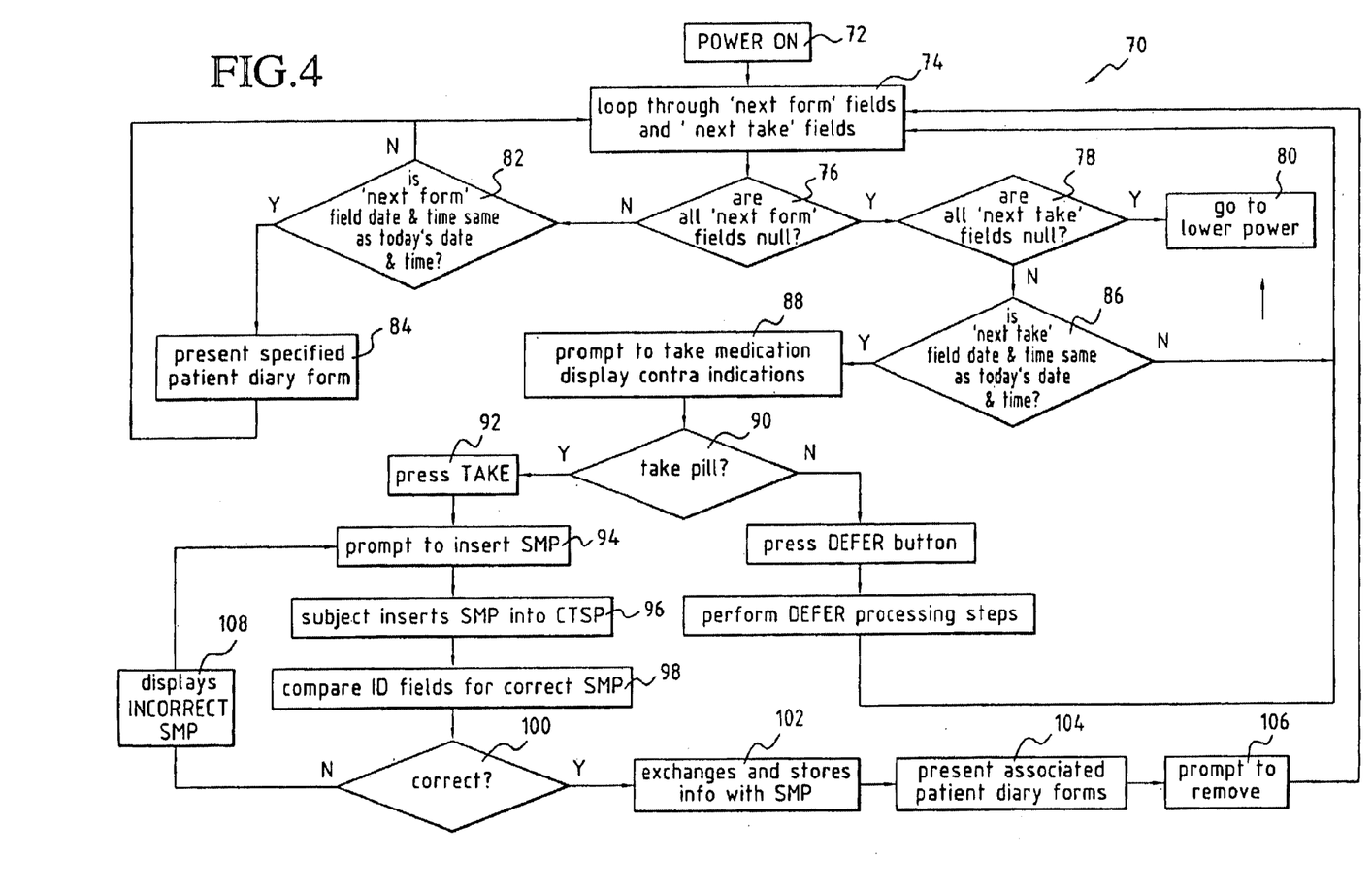
FIG. 4 is a flowchart showing clinical trial subject prompter operating system initiated operation.

Referring to FIG. 4 the logic steps of the CTSP to prompt the patient or consumer is shown generally at 70. For the CTSP system to be in the active mode the power is on 72. CTSP system loops 74 through the "next take" fields and "next form fields". CTSP system determines if all the "next form" fields are null 76. If no, CTSP system determines if the date and time in the "next form" field is the same as the current date and time 82. If yes, then CTSP system presents the specific patient diary form 84. There after the system goes back to loop 74. If the date and time is not the same then the system goes back to loop 74. If the "next form" fields are null, that is there is no information in the "next form" fields, CTSP system determines if the "next take" fields are null 78. If the "next form" fields are null the system goes to lower power 80. On the other hand, if the "next take" field is not null, that is there is information in the "next take" field, then is the date and time in the "next take" field is the same as the current date and time 86. If no, then return to loop 74. If yes, then the CTSP system prompts to take the medication and displays contra indications 88. The prompt may be an audio prompt, a vibration or a visual prompt or a combination thereof. The patient then decides 90 either to take the pill immediately or to defer taking the pill. If the patient chooses to take the medication, then the patient presses TAKE 92. CTSP system prompts 94 the consumer to insert a specific smart medication package (SMP) which has a smart memory associated therewith. Thereafter the subject "inserts" the SMP into the CTSP 96. Inserting means that the medication package is brought into proximity with the CTSP such that the smart memory attached to the package may be read by the CTSP. CTSP system compares 98 the identifier in the smart memory with the identifier associated with the "next take" field. If the identifiers are correct 100, information regarding the date and time is exchanged and stored 102. That is, the next take time is calculated and stored. Information regarding the date and time of the patient taking the medication may be stored on the medication package as well as the CTSP system. Thereafter a patient diary form may be presented 104. It will be appreciated that it is determined by the CRC when the patient diary form is presented and most likely it will be presented at the time of taking the medication and it may also be presented at other times such as in the morning, at noon and at bed time. Thereafter, CTSP system prompts the patient to remove 106 the SMP and then goes back to loop 74. However, if the identifiers are incorrect, the message INCORRECT is displayed 108 and the device goes back to prompt 94 the subject to insert an SMP. If the patient cannot take the medication at the time of being prompted, the consumer may press the DEFER button 110. Thereafter the defer processing steps are performed 112 which include updating the date and time for the "next take" field. Thereafter the device goes back to the loop 74 regarding the "next take" and "next form" fields.

Figure 5:
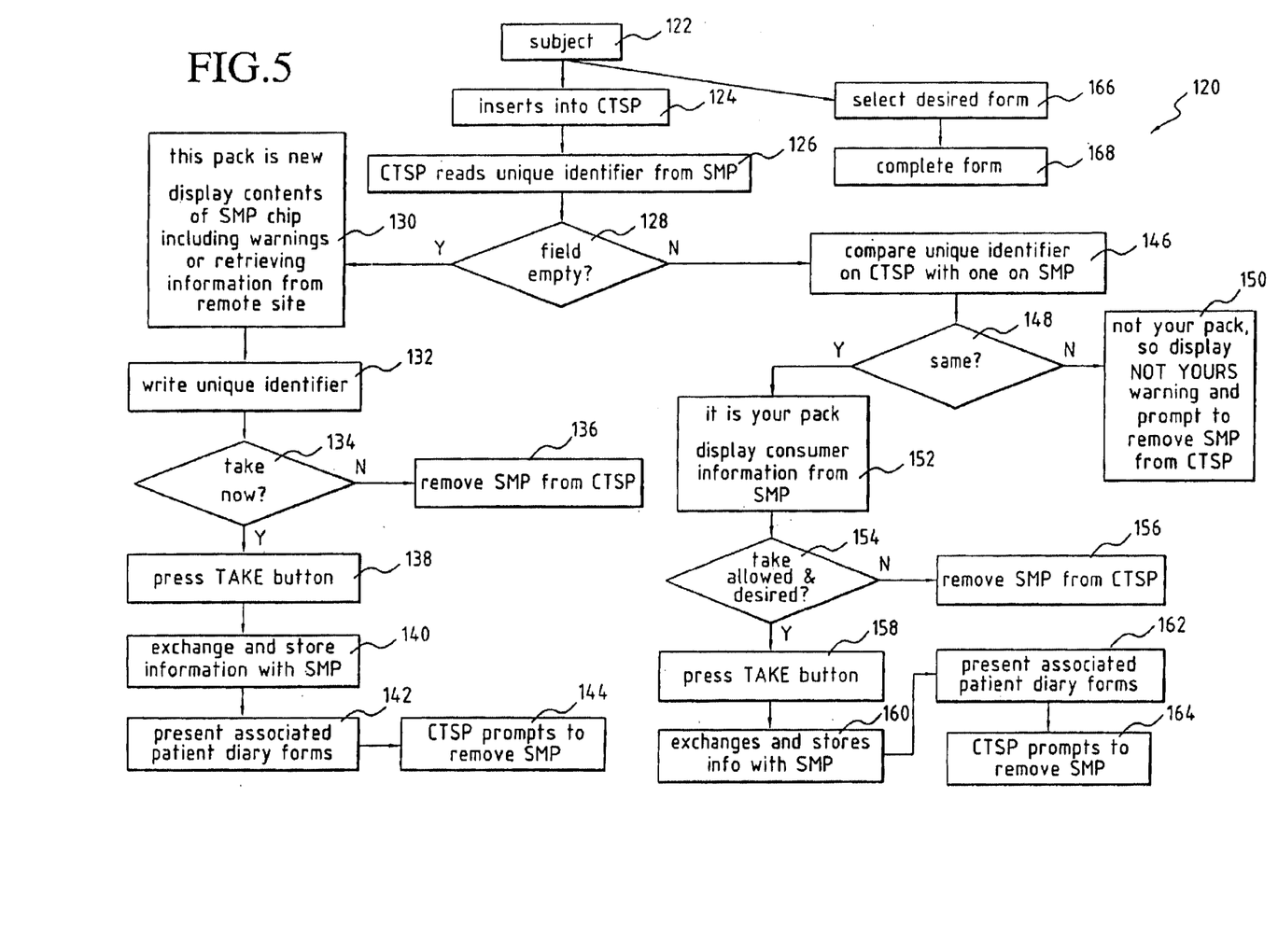
FIG. 5 is a flowchart showing clinical trial subject prompter trial subject initiated operation.

Referring to FIG. 5 the steps for the subject to initiate the operation of the CTSP are shown generally at 120. The subject 122 inserts 124 the SMP into the CTSP. As above the use of the word "insert" includes the SMP is brought into proximity with the CTSP system such that the information on the smart memory associated with the SMP can be read and information can be written thereto. The CTSP system reads the unique identifier 126 on the smart memory attached to the SMP. The CTSP system determines if the field is empty 128. If the field is empty it is a new package and the information in the smart memory is then read (or as discussed previously retrieved from a remote site) and displayed 130, including such information as best practices with regard to taking the medication, contra indicators and hazards. In addition, a unique identifier is written 132 onto the smart memory of the SMP. The CTSP system displays initiating steps for compliance 134. As discussed above this information could also be on a remote site that is pointed to by a pointer. If the patient decides not to take the medication, the package is removed 136 from the CTSP system. If the patient intends to take the medication now, the TAKE button is pressed 138, information regarding the taking of the medication is exchanged 140 between the CTSP system and the smart memory on the SMP. As well, the next take time is calculated and stored. Information regarding the date and time of the patient taking the medication is stored. In addition, a patient diary form is optionally presented 142. It wilt be appreciated by those skilled in the art that the patient diary form need not be presented at the time of taking the medication as discussed above with reference to FIG. 4. Thereafter the subject is prompted 144 to remove the package from CTSP system. On the other hand if the unique identifier field is not empty, the CTSP system compares 146 the unique identifier with identifier stored on the CTSP system. The CTSP system determines if it is the same identifier 148. If it is not the same, then the SMP with the smart memory is not for use in association with that particular CTSP system and it will display 150 "NOT YOURS" and prompt for the package to be removed from CTSP system. Alternatively, if the identifiers are the same 152 it is a package that is to be used in association with that particular CTSP system and information stored on the smart memory on the SMP is displayed, Preferably the information displayed includes the drug name, the next take time and if the time is currently within the take window, best practices, contra indicators, hazards, prescribing physician and the like. Thereafter the CTSP system determines if the current time is within the allowable "next take" time 154. If no, then the system prompts the subject to remove 156 the SMP. If yes and the patient intends to take the medication, the TAKE button is pressed 158, information regarding the taking of the medication is exchanged 160 between the CTSP system and the smart memory on the SMP. As well, the next take time is calculated and stored. Information regarding the date and time of the patient taking the medication is stored. In addition, a patient diary form is optionally presented 162. Thereafter the subject is prompted 164 to remove the package from CTSP system. Alternatively it the subject 122 merely wants to record data, the subject selects 166 the preferred form and then completes the form 168.

Figure 6:
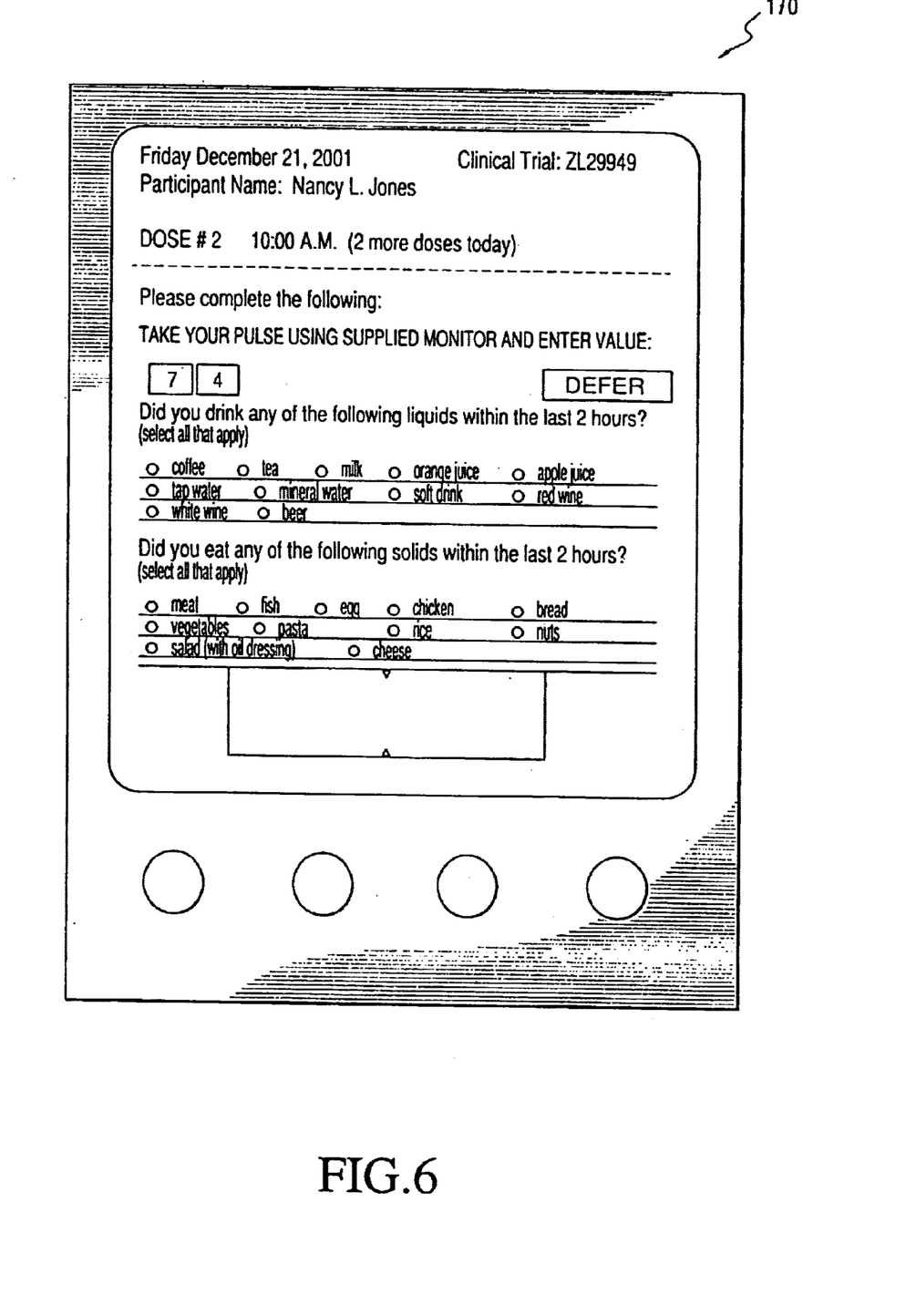
FIG. 6 is drawing showing a clinical trial subject prompter (as a typical PDA) with a patient diary form on the screen (text & graphics)

Referring to FIG. 6 a sample patient diary form is shown generally at 170. It will be appreciated by those skilled in the art that the patient diary forms may vary greatly depending on the needs of the CRCs. Further the patient diary forms may vary depending on the platform that is used.

Further it will be appreciated that the information gathered by the CTSP may be stored in a variety of ways. For example it may be on a database on the CTSP; on a smart card inserted into the CTSP (contact or contactless); on the smart medication package label itself (the advantage of this for subjects in remote locations is that the resulting trial data could be mailed to the trial site by simply mailing the package); and/or transmitted directly to the trial site host computers via a wireless telephony connection. Once the data from patient diaries collected on the CTSP is integrated into CRF collected data on a clinical trial data management system, queries can be constructed to support analysis. Further, data from patient diaries could also be collected when desired from CTSPs if they are on a platform that permits a wireless connection (e.g. if the platform was a 3G or greater cell phone, which maintains a continuous connection to the wireless network, the data could be retrieved virtually at any time).

It will be appreciated that the above description is related to the invention by way of example only. Many variations on the invention will be obvious to those skilled in the art and such obvious variations are within the scope of the invention as described herein whether or not expressly described.

What is claimed as the invention:

1. A method for use in association with clinical trials for a medication using a unique identifier, a clock and a smart memory associated with the medication comprising the steps of:
   determining if an identifier field on the smart memory associated with the medication is empty and, a) if empty, proceeding with a setup routine, b) if not empty, i) determining if the identifier in the identifier field is not the unique identifier then exiting; or ii) if the unique identifier is present in the identifier field:
   receiving information regarding a method of calculating a next take time;
   calculating the next take time;
   storing a next take time;
   prompting at the next take time;
   storing the time on the clock as a take time;
   displaying a subject diary form; and
   storing subject information in regard to the subject diary form.

2. A method as claimed in claim 1 wherein the subject diary forms are displayed at a time proximate to a time at which the next take time is prompted.

3. A method as claimed in claim 1 wherein the subject diary forms are displayed at predetermined times.

4. A method as claimed in claim 1 further including the step of receiving an indicator regarding taking the medication prior to the step of storing the time on the clock as a take time.

5. A method as claimed in claim 1 further including the steps of calculating a next take window and identifying if the present time is within the next take window.

6. A method as claimed in claim 1 further including the steps of calculating a deferred next take time and prompting at the deferred next take time.

7. A method as claimed in claim 1 further including the step of reading and displaying further information stored on the smart memory associated with the promoting device.

8. A method as claimed in claim 1 wherein the method is incorporated in one of an electronic personal organizer, a cell phone, a personal digital assistant and a hand held computer.

9. A method as claimed in claim 1 further including the following steps;
   determining if the next form field is null; if yes then determining if the next take field it null; if yes then exiting;
   if the next form field is not null then determining if the next form field date and time correspond to the clock date and time; if yes then displaying the patient diary form; if no then return to beginning; and
   if the next take field is not null then determining if the next take field date and time correspond to the clock date and time; if yes then prompting; if no then return to beginning.

10. A method as claimed in claim 1 wherein the take time and the patient information is stored on one of the smart memory associated with the medication and a smart card.

11. A method as claimed in claim 1 wherein the take time and the patient information is stored on both the smart memory associated with the medication and a smart card.

12. A method as claimed in claim 1 further including the step of loading the subject diary form from one of a subject smart card, the smart memory associated with the medication, a remote site via a pointer on a subject smart card and a remote site via a pointer on the smart memory associated with the medication.

13. A method as claimed in claim 2 wherein the subject diary forms are additionally displayed at predetermined times.

14. A method as claimed in claim 13 further including the step of receiving an indicator regarding taking the medication prior to the step of storing the time on the clock as a take time.

15. A method as claimed in claim 14 further including the following steps;
   determining if the next form field is null; if yes then determining if the next take field it null; if yes then exiting;
   if the next form field is not null then determining if the next form field date and time correspond to the clock date and time; if yes then displaying the patient diary form; if no then return to beginning; and
   if the next take field is not null then determining if the next take field date and time correspond to the clock date and time; if yes then prompting; if no then return to beginning.

16. A method as claimed in claim 15 further including the steps of calculating a next take window and identifying if the present time is within the next take window.

17. A method as claimed in claim 16 further including the steps of calculating a deferred next take time and prompting at the deferred next take time.

18. A method as claimed in claim 17 further including the step of reading and displaying further information stored on the smart memory on the prompting device.

19. A method as claimed in claim 18 wherein the take time and the patient information is stored on one of the smart memory associated with the medication and a smart card.

20. A method as claimed in claim 19 wherein the take time and the patient information is stored on both the smart memory associated with the medication and a smart card.

21. A method as claimed in claim 20 further including the step of loading the subject diary form from one of a subject smart card, the smart memory associated with the medication, a remote site via a pointer on a subject smart card and a remote site via a pointer on the smart memory associated with the medication.

22. A method as claimed in claim 1 wherein the setup routine includes the steps of:
   writing the unique identifier onto the smart memory;
   determining if taking now, if no then exiting, if yes then:
      receiving information regarding a method of calculating a next take time;
      calculating the next take time;
      storing a next take time;
      prompting at the next take time;
      storing the time on the clock as a take time;
      displaying a subject diary form; and
      storing subject information in regard to the subject diary form.

23. A method as claimed in claim 1 wherein the subject diary forms are displayed responsive to a request.

* * * * *